(12) United States Patent
Malackowski

(10) Patent No.: US 11,806,089 B2
(45) Date of Patent: *Nov. 7, 2023

(54) MERGING LOCALIZATION AND VISION DATA FOR ROBOTIC CONTROL

(71) Applicant: Stryker Corporation, Kalamazoo, MI (US)

(72) Inventor: Donald W. Malackowski, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 167 days.

This patent is subject to a terminal disclaimer.

(21) Appl. No.: 17/376,594

(22) Filed: Jul. 15, 2021

(65) Prior Publication Data

US 2021/0338341 A1 Nov. 4, 2021

Related U.S. Application Data

(63) Continuation of application No. 16/880,335, filed on May 21, 2020, now Pat. No. 11,103,315, which is a
(Continued)

(51) Int. Cl.
*A61B 34/20* (2016.01)
*A61B 34/30* (2016.01)
(Continued)

(52) U.S. Cl.
CPC .............. *A61B 34/20* (2016.02); *A61B 5/065* (2013.01); *A61B 34/30* (2016.02); *A61B 90/361* (2016.02);
(Continued)

(58) Field of Classification Search
CPC .. A61B 2017/00734; A61B 2034/2048; A61B 2034/2051; A61B 2034/2055;
(Continued)

(56) References Cited

U.S. PATENT DOCUMENTS 4,962,463 A 10/1990 Crossno et al.
5,603,318 A 2/1997 Heilbrun et al.
(Continued)

FOREIGN PATENT DOCUMENTS

CN 101254103 A 9/2008
DE 19639615 C2 10/1999
(Continued)

OTHER PUBLICATIONS

Abovitz, R., Digital surgery the future of medicine and human-robot symbiotic interaction, Industrial Robot: An International Journal, 2001, pp. 401-406, vol. 28, Issue 5, Hollywood, FL, USA; 5 pages.
(Continued)

*Primary Examiner* — Jon Eric C Morales
(74) *Attorney, Agent, or Firm* — Howard & Howard Attorneys PLLC

(57) ABSTRACT

Surgical systems and methods are described in which a localizer generates localizer data associated with a bone. A vision device generates, in a coordinate system of the vision device, image data associated with the bone and an environment of the bone within a field-of-view of the vision device. A robotic manipulator supports and moves a surgical instrument. Controller(s) associate a virtual object with the bone and determine a position and orientation of the virtual object based on the localizer data. Controller(s) merge the image data and the localizer data associated with the bone into a common coordinate system and control the robotic manipulator based on an output of merging the image data and the localizer data.

20 Claims, 5 Drawing Sheets

Related U.S. Application Data continuation of application No. 15/393,876, filed on Dec. 29, 2016, now Pat. No. 10,667,868.

(60) Provisional application No. 62/273,543, filed on Dec. 31, 2015.

(51) Int. Cl.
*A61B 90/00* (2016.01)
*A61B 5/06* (2006.01)
*A61B 17/00* (2006.01)

(52) U.S. Cl.
CPC .............. *A61B 2017/00734* (2013.01); *A61B 2034/2048* (2016.02); *A61B 2034/2051* (2016.02); *A61B 2034/2055* (2016.02); *A61B 2034/2068* (2016.02); *A61B 2034/2072* (2016.02); *A61B 2090/364* (2016.02); *A61B 2090/3937* (2016.02); *A61B 2090/3945* (2016.02)

(58) Field of Classification Search
CPC .... A61B 2034/2068; A61B 2034/2072; A61B 2090/364; A61B 2090/3937; A61B 2090/3945; A61B 34/20; A61B 34/30; A61B 5/065; A61B 90/361
See application file for complete search history.

(56) References Cited

U.S. PATENT DOCUMENTS

| | | |
|---|---|---|
| 5,715,836 A | 2/1998 | Kliegis et al. |
| 5,765,561 A | 6/1998 | Chen et al. |
| 5,817,005 A | 10/1998 | Cohen |
| 5,820,623 A | 10/1998 | Ng |
| 5,824,085 A | 10/1998 | Sahay et al. |
| 5,871,018 A | 2/1999 | Delp et al. |
| 5,880,976 A | 3/1999 | DiGioia III et al. |
| 5,882,206 A | 3/1999 | Gillio |
| 5,891,157 A | 4/1999 | Day et al. |
| 5,950,629 A | 9/1999 | Taylor et al. |
| 5,952,796 A | 9/1999 | Colgate et al. |
| 5,971,976 A | 10/1999 | Wang et al. |
| 5,976,156 A | 11/1999 | Taylor et al. |
| 5,995,738 A | 11/1999 | DiGioia, III et al. |
| 6,002,859 A | 12/1999 | DiGioia, III et al. |
| 6,021,343 A | 2/2000 | Foley et al. |
| 6,033,415 A | 3/2000 | Mittelstadt et al. |
| 6,037,927 A | 3/2000 | Rosenberg |
| 6,063,095 A | 5/2000 | Wang et al. |
| 6,097,168 A | 8/2000 | Katoh et al. |
| 6,102,850 A | 8/2000 | Wang et al. |
| 6,157,873 A | 12/2000 | DeCamp et al. |
| 6,205,411 B1 | 3/2001 | DiGioia, III et al. |
| 6,228,089 B1 | 5/2001 | Wahrburg |
| 6,233,504 B1 | 5/2001 | Das et al. |
| 6,236,875 B1 | 5/2001 | Bucholz et al. |
| 6,236,906 B1 | 5/2001 | Muller |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,341,231 B1 | 1/2002 | Ferre et al. |
| 6,347,240 B1 | 2/2002 | Foley et al. |
| 6,351,659 B1 | 2/2002 | Vilsmeier |
| 6,351,661 B1 | 2/2002 | Cosman |
| 6,368,330 B1 | 4/2002 | Hynes et al. |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,405,072 B1 | 6/2002 | Cosman |
| 6,408,253 B2 | 6/2002 | Rosenberg et al. |
| 6,413,264 B1 | 7/2002 | Jensen et al. |
| 6,414,711 B2 | 7/2002 | Arimatsu et al. |
| 6,421,048 B1 | 7/2002 | Shih et al. |
| 6,423,077 B2 | 7/2002 | Carol et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,434,507 B1 | 8/2002 | Clayton et al. |
| 6,436,107 B1 | 8/2002 | Wang et al. |
| 6,450,978 B1 | 9/2002 | Brosseau et al. |
| 6,456,868 B2 | 9/2002 | Saito et al. |
| 6,461,372 B1 | 10/2002 | Jensen et al. |
| 6,466,815 B1 | 10/2002 | Saito et al. |
| 6,473,635 B1 | 10/2002 | Rasche |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,511,418 B2 | 1/2003 | Shahidi et al. |
| 6,514,082 B2 | 2/2003 | Kaufman et al. |
| 6,514,259 B2 | 2/2003 | Picard et al. |
| 6,520,228 B1 | 2/2003 | Kennedy et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,620,174 B2 | 9/2003 | Jensen et al. |
| 6,665,554 B1 | 12/2003 | Charles et al. |
| 6,676,669 B2 | 1/2004 | Charles et al. |
| 6,699,177 B1 | 3/2004 | Wang et al. |
| 6,704,694 B1 | 3/2004 | Basdogan et al. |
| 6,711,432 B1 | 3/2004 | Krause et al. |
| 6,723,106 B1 | 4/2004 | Charles et al. |
| 6,724,922 B1 | 4/2004 | Vilsmeier |
| 6,728,599 B2 | 4/2004 | Wang et al. |
| 6,757,416 B2 | 6/2004 | Kleiman et al. |
| 6,757,582 B2 | 6/2004 | Brisson et al. |
| 6,778,867 B1 | 8/2004 | Ziegler et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,804,547 B2 | 10/2004 | Pelzer et al. |
| 6,815,659 B2 | 11/2004 | Cartlidge |
| 6,827,723 B2 | 12/2004 | Carson |
| 6,837,892 B2 | 1/2005 | Shoham |
| 6,850,794 B2 | 2/2005 | Shahidi |
| 6,858,003 B2 | 2/2005 | Evans et al. |
| 6,871,117 B2 | 3/2005 | Wang et al. |
| 6,892,112 B2 | 5/2005 | Wang et al. |
| 6,929,606 B2 | 8/2005 | Ritland |
| 6,951,538 B2 | 10/2005 | Ritland |
| 6,963,792 B1 | 11/2005 | Green |
| 6,978,166 B2 | 12/2005 | Foley et al. |
| 6,999,852 B2 | 2/2006 | Green |
| 7,006,895 B2 | 2/2006 | Green |
| 7,035,716 B2 | 4/2006 | Harris et al. |
| 7,043,961 B2 | 5/2006 | Pandey et al. |
| 7,050,845 B2 | 5/2006 | Vilsmeier |
| 7,055,789 B2 | 6/2006 | Libbey et al. |
| 7,056,123 B2 | 6/2006 | Gregorio et al. |
| 7,097,640 B2 | 8/2006 | Wang et al. |
| 7,139,601 B2 | 11/2006 | Bucholz et al. |
| 7,155,316 B2 | 12/2006 | Sutherland et al. |
| 7,158,736 B2 | 1/2007 | Sato et al. |
| 7,166,114 B2 | 1/2007 | Moctezuma De La Barrera et al. |
| 7,181,315 B2 | 2/2007 | Watanabe et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,215,326 B2 | 5/2007 | Rosenberg |
| 7,239,940 B2 | 7/2007 | Wang et al. |
| 7,249,951 B2 | 7/2007 | Bevirt et al. |
| 7,346,417 B2 | 3/2008 | Luth et al. |
| 7,404,716 B2 | 7/2008 | Gregorio et al. |
| 7,454,268 B2 | 11/2008 | Jinno |
| 7,466,303 B2 | 12/2008 | Yi et al. |
| 7,468,594 B2 | 12/2008 | Svensson et al. |

(56) References Cited

U.S. PATENT DOCUMENTS

| | | | |
|---|---|---|---|
| 7,492,930 B2 | 2/2009 | Leitner et al. |
| 7,543,588 B2 | 6/2009 | Wang et al. |
| 7,561,733 B2 | 7/2009 | Vilsmeier et al. |
| 7,573,461 B2 | 8/2009 | Rosenberg |
| 7,625,383 B2 | 12/2009 | Charles et al. |
| 7,630,753 B2 | 12/2009 | Simon et al. |
| 7,648,513 B2 | 1/2010 | Green et al. |
| 7,660,623 B2 | 2/2010 | Hunter et al. |
| 7,683,565 B2 | 3/2010 | Quaid et al. |
| 7,725,162 B2 | 5/2010 | Malackowski et al. |
| 7,726,564 B2 | 6/2010 | Goldbach |
| 7,744,608 B2 | 6/2010 | Lee et al. |
| 7,747,311 B2 | 6/2010 | Quaid, III |
| 7,747,312 B2 | 6/2010 | Barrick et al. |
| 7,772,541 B2 | 8/2010 | Froggatt et al. |
| 7,801,342 B2 | 9/2010 | Boese et al. |
| 7,813,838 B2 | 10/2010 | Sommer |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |
| 7,840,253 B2 | 11/2010 | Tremblay et al. |
| 7,892,243 B2 | 2/2011 | Stuart |
| 7,914,522 B2 | 3/2011 | Morley et al. |
| 7,950,306 B2 | 5/2011 | Stuart |
| 7,967,742 B2 | 6/2011 | Hoeg et al. |
| 7,987,001 B2 | 7/2011 | Feichman et al. |
| 8,010,180 B2 | 8/2011 | Quaid et al. |
| 8,027,526 B2 | 9/2011 | Boese et al. |
| 8,041,459 B2 | 10/2011 | Sutherland et al. |
| 8,187,180 B2 | 5/2012 | Pacey |
| 8,287,522 B2 | 10/2012 | Moses et al. |
| 8,320,612 B2 | 11/2012 | Knobel et al. |
| 8,343,048 B2 | 1/2013 | Warren, Jr. |
| 8,382,372 B2 | 2/2013 | Maschke |
| 8,442,621 B2 | 5/2013 | Gorek et al. |
| 8,792,963 B2 | 7/2014 | Zhao et al. |
| 8,838,205 B2 | 9/2014 | Shoham et al. |
| 8,945,140 B2 | 2/2015 | Hubschman et al. |
| 8,954,132 B2 | 2/2015 | Hubschman et al. |
| 8,974,380 B2 | 3/2015 | Michaeli et al. |
| 9,002,432 B2 | 4/2015 | Feilkas |
| 9,008,757 B2 | 4/2015 | Wu |
| 9,044,257 B2 | 6/2015 | Fielding et al. |
| 9,119,638 B2 | 9/2015 | Schwarz et al. |
| 9,119,655 B2 | 9/2015 | Bowling et al. |
| 9,119,670 B2 | 9/2015 | Yang et al. |
| 9,168,104 B2 | 10/2015 | Dein |
| 9,188,973 B2 | 11/2015 | Tenney et al. |
| 9,283,048 B2 | 3/2016 | Kostrzewski et al. |
| 9,307,969 B2 | 4/2016 | Novak et al. |
| 9,381,085 B2 | 7/2016 | Axelson, Jr. et al. |
| 9,402,691 B2 | 8/2016 | Merritt et al. |
| 9,420,944 B2 | 8/2016 | Sutherland et al. |
| 9,480,534 B2 | 11/2016 | Bowling et al. |
| 9,492,240 B2 | 11/2016 | Itkowitz et al. |
| 9,510,771 B1 | 12/2016 | Finley et al. |
| 9,510,914 B2 | 12/2016 | Yang et al. |
| 9,542,743 B2 | 1/2017 | Tenney et al. |
| 9,566,052 B2 | 2/2017 | Novak |
| 9,566,120 B2 | 2/2017 | Malackowski et al. |
| 9,603,665 B2 | 3/2017 | Bowling et al. |
| 9,615,987 B2 | 4/2017 | Worm et al. |
| 9,629,595 B2 | 4/2017 | Walker et al. |
| 9,642,606 B2 | 5/2017 | Charles et al. |
| 9,668,819 B2 | 6/2017 | Stolka |
| 9,681,796 B2 | 6/2017 | Tesar et al. |
| 9,707,043 B2 | 7/2017 | Bozung |
| 9,718,190 B2 | 8/2017 | Larkin et al. |
| 9,733,336 B2 | 8/2017 | Shen et al. |
| 9,733,463 B2 | 8/2017 | Eslami et al. |
| RE46,562 E | 10/2017 | Huennekens et al. |
| 9,833,254 B1 | 12/2017 | Barral et al. |
| 9,867,531 B2 | 1/2018 | Pacey et al. |
| 9,901,408 B2 | 2/2018 | Larkin |
| 9,901,409 B2 | 2/2018 | Yang et al. |
| 9,933,606 B2 | 4/2018 | Saur et al. |
| 9,987,093 B2 | 6/2018 | Christian et al. |
| 10,039,474 B2 | 8/2018 | Taylor et al. |
| 10,045,882 B2 | 8/2018 | Balicki et al. |
| 10,064,691 B2 | 9/2018 | Frimer et al. |
| 10,154,882 B2 | 12/2018 | Garbey et al. |
| 10,159,532 B1 | 12/2018 | Ummalaneni |
| 10,165,981 B2 | 1/2019 | Schoepp |
| 10,178,368 B2 | 1/2019 | Zhao et al. |
| 10,247,545 B2 | 4/2019 | Elliot |
| 10,512,509 B2 | 12/2019 | Bowling et al. |
| 10,667,868 B2 * | 6/2020 | Malackowski | A61B 34/30 |
| 11,103,315 B2 * | 8/2021 | Malackowski | A61B 34/20 |
| 2002/0035321 A1 | 3/2002 | Bucholz et al. |
| 2002/0120188 A1 | 8/2002 | Brock et al. |
| 2003/0181800 A1 | 9/2003 | Bonutti |
| 2003/0208296 A1 | 11/2003 | Brisson et al. |
| 2004/0010190 A1 | 1/2004 | Shahidi |
| 2004/0024311 A1 | 2/2004 | Quaid |
| 2004/0034283 A1 | 2/2004 | Quaid |
| 2004/0034302 A1 | 2/2004 | Abovitz et al. |
| 2004/0059194 A1 | 3/2004 | Berg et al. |
| 2004/0077939 A1 | 4/2004 | Graumann |
| 2004/0106916 A1 | 6/2004 | Quaid et al. |
| 2004/0138556 A1 | 7/2004 | Cosman |
| 2005/0054895 A1 | 3/2005 | Hoeg et al. |
| 2005/0054897 A1 | 3/2005 | Hashimoto et al. |
| 2005/0143651 A1 | 6/2005 | Verard et al. |
| 2005/0171553 A1 | 8/2005 | Schwarz et al. |
| 2005/0203490 A1 | 9/2005 | Simonson |
| 2006/0020279 A1 | 1/2006 | Chauhan et al. |
| 2006/0109266 A1 | 5/2006 | Itkowitz et al. |
| 2006/0142657 A1 | 6/2006 | Quaid et al. |
| 2006/0155262 A1 | 7/2006 | Kishi et al. |
| 2006/0176242 A1 | 8/2006 | Jaramaz et al. |
| 2006/0258938 A1 | 11/2006 | Hoffman et al. |
| 2007/0135686 A1 | 6/2007 | Pruitt et al. |
| 2007/0183637 A1 | 8/2007 | Kreuzer et al. |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0287911 A1 | 12/2007 | Haid et al. |
| 2008/0021283 A1 | 1/2008 | Kuranda |
| 2008/0058776 A1 | 3/2008 | Jo et al. |
| 2008/0077158 A1 | 3/2008 | Haider et al. |
| 2008/0108912 A1 | 5/2008 | Node-Langlois |
| 2008/0161829 A1 | 7/2008 | Kang |
| 2008/0183068 A1 | 7/2008 | Carls et al. |
| 2008/0200794 A1 | 8/2008 | Feichman et al. |
| 2008/0214898 A1 | 9/2008 | Warren |
| 2008/0243142 A1 | 10/2008 | Gildenberg |
| 2008/0281989 A1 | 11/2008 | Hager et al. |
| 2009/0003975 A1 | 1/2009 | Kuduvalli et al. |
| 2009/0024140 A1 | 1/2009 | Allen et al. |
| 2009/0157059 A1 | 6/2009 | Allen et al. |
| 2010/0295931 A1 | 11/2010 | Schmidt |
| 2010/0331859 A1 | 12/2010 | Omori |
| 2011/0075912 A1 | 3/2011 | Rieber et al. |
| 2011/0106102 A1 | 5/2011 | Balicki et al. |
| 2011/0130761 A1 | 6/2011 | Plaskos et al. |
| 2011/0152676 A1 | 6/2011 | Groszmann et al. |
| 2011/0263971 A1 | 10/2011 | Nikou et al. |
| 2011/0264107 A1 | 10/2011 | Nikou et al. |
| 2012/0059378 A1 | 3/2012 | Farrell |
| 2012/0071752 A1 | 3/2012 | Sewell et al. |
| 2012/0071893 A1 | 3/2012 | Smith et al. |
| 2012/0143084 A1 | 6/2012 | Shoham |
| 2012/0190965 A1 | 7/2012 | Schaerer et al. |
| 2012/0330429 A1 | 12/2012 | Axelson, Jr. et al. |
| 2013/0006267 A1 | 1/2013 | Odermatt et al. |
| 2013/0019883 A1 | 1/2013 | Worm et al. |
| 2013/0060278 A1 | 3/2013 | Bozung et al. |
| 2013/0096574 A1 | 4/2013 | Kang et al. |
| 2014/0005684 A1 | 1/2014 | Kim et al. |
| 2014/0039681 A1 | 2/2014 | Bowling et al. |
| 2014/0107426 A1 | 4/2014 | Wilson |
| 2014/0171787 A1 | 6/2014 | Garbey et al. |
| 2014/0180290 A1 | 6/2014 | Otto et al. |

(56) References Cited

U.S. PATENT DOCUMENTS

| | | |
|---|---|---|
| 2014/0200621 A1 | 7/2014 | Malackowski et al. |
| 2014/0221822 A1 | 8/2014 | Ehlers et al. |
| 2014/0276943 A1 | 9/2014 | Bowling et al. |
| 2015/0005643 A1 | 1/2015 | Whitman et al. |
| 2015/0018622 A1 | 1/2015 | Tesar et al. |
| 2015/0265370 A1 | 9/2015 | Garbey et al. |
| 2015/0351860 A1 | 12/2015 | Piron et al. |
| 2016/0113728 A1 | 4/2016 | Piron et al. |
| 2016/0183911 A1 | 6/2016 | Waksman |
| 2016/0278864 A1 | 9/2016 | Paitel |
| 2016/0345917 A1 | 12/2016 | Daon et al. |
| 2017/0143429 A1 | 5/2017 | Richmond et al. |
| 2017/0143432 A1 | 5/2017 | Bowling et al. |
| 2017/0189125 A1 | 7/2017 | Malackowski |
| 2017/0209225 A1 | 7/2017 | Wu |
| 2017/0215857 A1 | 8/2017 | D'Urso |
| 2017/0238998 A1 | 8/2017 | Srimohanarajah et al. |
| 2017/0265947 A1 | 9/2017 | Dyer et al. |
| 2017/0281282 A1 | 10/2017 | Noonan et al. |
| 2017/0296162 A1 | 10/2017 | Wan |
| 2017/0312036 A1 | 11/2017 | Hoffman et al. |
| 2017/0325674 A1 | 11/2017 | Kleiner et al. |
| 2017/0333137 A1 | 11/2017 | Roessler |
| 2017/0358091 A1 | 12/2017 | Ekin |
| 2018/0078315 A1 | 3/2018 | Ren et al. |
| 2018/0116732 A1 | 5/2018 | Lin et al. |
| 2018/0147727 A1 | 5/2018 | Mewes et al. |
| 2018/0153626 A1 | 6/2018 | Yang et al. |
| 2018/0199951 A1 | 7/2018 | Chappuis et al. |
| 2018/0228553 A1 | 8/2018 | Bai et al. |
| 2018/0235715 A1 | 8/2018 | Amiot et al. |
| 2018/0303580 A1 | 10/2018 | Salah et al. |
| 2018/0311012 A1 | 11/2018 | Moctezuma et al. |
| 2018/0368929 A1 | 12/2018 | Popovic et al. |
| 2019/0050984 A1 | 2/2019 | Blendinger |
| 2019/0059833 A1 | 2/2019 | Govari |
| 2019/0069962 A1 | 3/2019 | Tabandeh et al. |
| 2020/0030046 A1 | 1/2020 | Bowling et al. |
| 2020/0085513 A1 | 3/2020 | Bowling et al. |
| 2020/0100849 A1 | 4/2020 | Malackowski et al. |
| 2020/0281663 A1 | 9/2020 | Malackowski |

FOREIGN PATENT DOCUMENTS

| | | |
|---|---|---|
| EP | 0685088 B1 | 9/2000 |
| EP | 1321105 B1 | 8/2003 |
| EP | 1545368 B1 | 3/2009 |
| EP | 3449859 A1 | 3/2019 |
| JP | 2005532890 A | 11/2005 |
| JP | 2006106419 A | 4/2006 |
| KR | 20100098055 A | 9/2010 |
| KR | 20110036453 A | 4/2011 |
| WO | 199611624 A2 | 4/1996 |
| WO | 1999037220 A1 | 7/1999 |
| WO | 2000021450 A1 | 4/2000 |
| WO | 2000035366 A1 | 6/2000 |
| WO | 2000059397 A1 | 10/2000 |
| WO | 2000060571 A1 | 10/2000 |
| WO | 2001003586 A1 | 1/2001 |
| WO | 200200131 A1 | 1/2002 |
| WO | 2002024051 A2 | 3/2002 |
| WO | 2002060653 A2 | 8/2002 |
| WO | 2002065931 A1 | 8/2002 |
| WO | 2002074500 A2 | 9/2002 |
| WO | 2002076302 A2 | 10/2002 |
| WO | 2003094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2006058633 A1 | 6/2006 |
| WO | 2006063156 A1 | 6/2006 |
| WO | 2006091494 A1 | 8/2006 |
| WO | 2006106419 A2 | 10/2006 |
| WO | 2007017642 A1 | 2/2007 |
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2009045827 A2 | 4/2009 |
| WO | 2009059330 A2 | 5/2009 |
| WO | 2011021192 A1 | 2/2011 |
| WO | 2011088541 A1 | 7/2011 |
| WO | 2011106861 A1 | 9/2011 |
| WO | 2011113483 A1 | 9/2011 |
| WO | 2011128766 A2 | 10/2011 |
| WO | 2011133873 A1 | 10/2011 |
| WO | 2011133927 A2 | 10/2011 |
| WO | 2011134083 A1 | 11/2011 |
| WO | 2012018816 A2 | 2/2012 |
| WO | 2013132501 A1 | 9/2013 |
| WO | 2015087218 A1 | 6/2015 |
| WO | 2015100310 A1 | 7/2015 |
| WO | 2017012624 A1 | 1/2017 |
| WO | 2017059870 A1 | 4/2017 |
| WO | 2017158592 A2 | 9/2017 |
| WO | 2017187795 A1 | 11/2017 |
| WO | 2017195192 A1 | 11/2017 |
| WO | 2017205351 A1 | 11/2017 |
| WO | 2018237187 A2 | 12/2018 |
| WO | 2018237187 A3 | 1/2019 |
| WO | 2019070729 A1 | 4/2019 |
| WO | 2019070997 A1 | 4/2019 |

OTHER PUBLICATIONS

Abovitz, R.A., Human-Interactive Medical Robotics, Abstract for CAOS 2000, 2000, pp. 71-72; 2 pages.

Ansar, Adnan, et al., Visual and haptic collaborative tele-presence. Computers & Graphics, 2001, pp. 789-798, vol. 25, Elsevier, Inc.; 10 pages.

Baerentzen, J. Andreas, Octree-based Volume Sculpting, Proc. Late Breaking Hot Topics, IEEE Visualization '98, pp. 9-12, 1998; 4 pages.

Bainville, E. et al., Concepts and Methods of Registration for Computer-Integrated Surgery, Computer Assisted Orthopedic Surgery (CAOS), 1999, pp. 15-34, Hogrefe & Huber Publishers, Bern.

Bargar, W.L. et al., Primary and Revision Total Hip Replacement Using the Robodoc System, Clinical Orthopaedics and Related Research, Sep. 1998, pp. 82-91, No. 354; 10 pages.

Bouazza-Marouf, K. et al., Robot-assisted invasive orthopaedic surgery, Mechatronics in Surgery, Jun. 1996, pp. 381-397, vol. 6, Issue 4, UK; 17 pages.

Brandt, G. et al., "CRIGOS: A Compact Robot for Image-Guided Orthopedic Surgery," Information Technology in Biomedicine, IEEE Transactions on, vol. 3, No. 4, pp. 252-260,Dec. 1999; 9 pages.

Brisson, G. et al., Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-VerlagBerlin Heidelberg 2004; 8 pages.

Buckingham, R.O., Robotics in surgery a new generation of surgical tools incorporate computer technology and mechanical actuation to give surgeons much finer control than previously possible during some operations, IEE Review, Sep. 1994, pp. 193-196; 4pages.

Buckingham, R.O., Safe Active Robotic Devices for Surgery, Systems, Man and Cybernetics, 1993. 'Systems Engineering in the Service of Humans', Conference Proceedings., International Conference on, Oct. 17-20, 1993, pp. 355-358, vol. 5, IEEE, LeTougeut; 4 pages.

Burghart, C.R. et al., A. Pernozzoli; H. Grabowski; J. Muenchenberg; J. Albers; S. Hafeld; C. Vahl; U. Rembold; H. Woern, Robot assisted craniofacial surgery first clinical evaluation, Computer Assisted Radiology andSurgery, 1999, pp. 828-833; 7 pages.

Burghart, C.R. et al., Robot Controlled Osteotomy in Craniofacial Surgery, First International Workshop on Haptic Devices in Medical Applications Proceedings, Jun. 23, 1999, pp. 12-22, Paris, FR; 13 pages.

(56) References Cited

OTHER PUBLICATIONS

Burghart, C.R., Robotergestulzle Osteotomie in der craniofacialen Chirurgie (Robot Clipped osteotomy in craniofacial surgery), Jul. 1, 1999, GCA-Verlag, 2000; 250 pages.

Choi, D.Y. et al., Flexure-based Manipulator for Active Handheld Microsurgical Instrument, Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005; 4 pages.

Colgate, J.E. et al., Issues in the Haptic Display of Tool Use, Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.

Davies, B.L. "Robotics in minimally invasive surgery, Through the Keyhole: Microengineering in Minimally Invasive Surgery", IEE Colloquium on, Jun. 6, 1995, p. 5/1-5/2, London, UK; 2 pages.

Davies, B.L. et al., Acrobot-using robots and surgeons synergistically in knee surgery, Advanced Robotics, 1997. ICAR '97. Proceedings., 8th International Conference on, Jul. 7-9, 1997, pp. 173-178, IEEE, Monterey, CA, USA; 6 pages.

Davies, B.L. et al., Active compliance in robotic surgery—the use of force control as a dynamic constraint, Proceedings of the Institution of Mechanical Engineers, Part H: Journal of Engineeringin Medicine, Apr. 1, 1997, pp. 285-292, vol. 211, Sage; 9 pages.

Davies, B.L. et al., Neurobot a special-purpose robot for neurosurgery, Robotics and Automation, 2000. Proceedings. ICRA '00. IEEE International Conference on, Apr. 2000, pp. 4103-4108, vol. 4,IEEE, San Francisco, CA, USA; 6 pages.

Davies, B.L., A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.

Davies, B.L., Computer-assisted and robotics surgery, International Congress and Symposium Series 223, 1997, pp. 71-82, Royal Society of Medicine Press Limited; 12 pages.

Delp, S.L. et al., Computer Assisted Knee Replacement, Clinical Orthopaedics, Sep. 1998, pp. 49-56, vol. 354, Lippincott-Raven Publishers; 8 pages.

Digioia,A.M. et al., "Computer Assisted Orthopaedic Surgery Image Guided and Robotic Assistive Technologies, Clinical Orthopaedics & Related Research":. Sep. 1998, pp. 8-16, vol. 354, Lippincott Williams & Wilkins, Pittsburgh, PA, USA; 9 pages.

Doignon, C. et al., "Segmentation and guidance of multiple rigid objects for intra-operative endoscopic vision", Proceeding WDV'05/WDV'06/ICCV'05/ECCV'06 Proceedings of the 2005/2006 International Conference on Dynamical Vision,2006, pp. 314-327, Springer-Verlag Berlin, Heidelberg, lllkirch, FR; 14 pages.

Ellis, R.E. et al., A surgical planning and guidance system for high tibial osteotomy, Computer Aided Surgery, Apr. 16, 1999, 264-274, vol. 4, Wiley-Liss, Inc.; 11 pages.

Engel, D. et al., A Safe Robot System for Craniofacial Surgery, Robotics and Automation, 2001. Proceedings 2001 ICRA IEEE International Conference on (vol. 2), pp. 2020-2024, IEEE; 5 pages.

English language abstract and machine-assisted English translation for DE 196 39 615 extracted from espacenet.com database on Nov. 29, 2018, 26 pages.

English language abstract and machine-assisted English translation for KR 2010-0098055 extracted from espacenet.com database on Jun. 27, 2019, 14 pages.

English language abstract and machine-assisted English translation for KR 2011-0036453 extracted from espacenet.com database on Jun. 27, 2019, 31 pages.

English language abstract and machine-assisted English translation for WO 2000/021450 extracted from espacenet.com database on Jul. 3, 2014, 11 pages.

English language abstract and machine-assisted English translation for WO 2002/065931 extracted from espacenet.com database on Aug. 11, 2014, 8 pages.

English language abstract and machine-assisted English translation for WO 2002/074500 extracted from espacenet.com database on Aug. 11, 2014, 8 pages.

English language abstract for CN 101254103 extracted from espacenet.com database on Sep. 25, 2017, 2 pages.

English language abstract for EP 1 321 105 extracted from espacenet.com database on Nov. 29, 2018, 2 pages.

English language abstract for JP 2005-532890 extracted from espacenet.com database on Feb. 8, 2018, 1 page.

English language abstract for JP 2006-106419 extracted from espacenet.com database on Feb. 8, 2018, 1 page.

English language abstract for WO 2002/076302 extracted from espacenet.com database on Aug. 13, 2014, 2 pages.

English language abstract for WO 2004/019785 extracted from espacenet.com database on Aug. 13, 2014, 2 pages.

English language abstract for WO 2006/058633 extracted from espacenet.com database on Aug. 13, 2014, 2 pages.

English language abstract for WO 2017/187795 extracted from espacenet.com database on Jun. 20, 2019, 2 pages.

English language abstract not found for EP 0 685 088; however, see English language equivalent U.S. Pat. No. 5,715,836. Original document extracted from espacenet com database on Nov. 29, 2018, 13 pages.

Fadda, M. et al., "Premiers Pas Vers La Dissectomie et la Realisation de Protheses du Genou a L'Aide de Robots", Innov. Tech. Bio. Med. , 1992, pp. 394-409, vol. 13, No. 4; 16 pages.

Fadda, M. et al., Computer Assisted Planning for Total Knee Arthroplasty, 1997, pp. 619-628; 10 pages.

Fadda,M. et al., "Computer-Assisted Knee Arthroplasty at Rizzoli Institutes", First International Symposium on Medical Robotics and ComputerAssisted Surgery, Sep. 22-24, 1994, pp. 26-30, Pittsburgh, Pennsylvania, US; 6 pages.

Fluete, M. et al., Incorporating a statistically based shape model into a system for computer-assisted anterior cruciate ligament surgery, Medical Image Analysis, Oct. 1999, pp. 209-222, vol. 3, No. 3, FR; 14 pages.

Grueneis, C.O.R. et al., "Clinical Introduction of the Caspar System Problems and Initial Results", 4th International Symposium of Computer Assited Orthopaedic Surgery, CAOS'99, Abstracts from CAOS '99, 1999, p. 160, Davos, Switzerland; 1 page.

Haider, H. et al., Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.

Harris, S.J. et al., Experiences with Robotic Systems for Knee Surgery, CVRMed-MRCAS'97, Lecture Notes in Computer Science, 1997, pp. 757-766, vol. 1205, Springer Berlin Heidelberg,London, UK; 10 pages.

Harris, S.J. et al., Intra-operative Application of a Robotic Knee Surgery System, Medical Image Computing and Computer-Assisted Intervention—MICCAI'99, 1999, pp. 1116-1124, vol. 1679, Springer-Verlag Berlin Heidelberg; 9pages.

Taylor, R.H. et al., An Image-Directed Robotic System for Precise Orthopaedic Surgery, Robotics and Automation, IEEE Transactions on,Jun. 1994, pp. 261-275, vol. 10, Issue 3, IEEE; 15 pages.

Taylor, R.H. et al., "A Model-Based Optimal Planning and Execution System with Active Sensing and Passive Manipulation for Augmentation of Human Precision in Computer-Integrated Surgery", Experimental Robotics II, The 2nd International Symposium, Lecture Notes in Control and Information Sciences, pp. 177-195, vol. 190, Springer Berlin Heidelberg, Toulouse, FR, Jun. 25-27, 1991; 19 p.

Tonet, O. et al., An Augmented Reality Navigation System for Computer Assisted Arthroscopic Surgery of the Knee, Medical Image Computing and Computer-AssistedIntervention—MICCAI 2000, Lecture Notes in Computer Science, 2000, pp. 1158-1162, vol. 1935, Springer Berlin Heidelberg; 5 pages.

Troccaz, J. et al., A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.

(56) References Cited

OTHER PUBLICATIONS

Troccaz, J. et al., Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages.

Troccaz, J. et al., Guiding systems for computer-assisted surgery introducing synergistic devices and discussing the different approaches, Medical Image Analysis, Jun. 1998, vol. 2, No. 2, pp. 101-119, Elsevier B.V.; 19 pages.

Van Ham, G. et al., Accuracy study on the registration of the tibia by means of an intramedullary rod in robot-assisted total knee arthroplasty, PosterSession—Knee Arthroplasty—Valencia Foyer, 46th Annual Meeting, Orthopaedic Research Society, Mar. 12-15, 2000, Orlando, Florida, Jan. 1, 2010, p. 450; 1 pages.

Van Ham, G. et al., Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

Wang, T et al.,"A robotized surgeon assistant, Intelligent Robots and Systems", 94. 'Advanced Robotic Systems and the Real World', IROS '94. Proceedings of the IEEE/RSJ/GI International Conference on,Sep. 12- 16, 1994, pp. 362-869, vol. 2, IEEE, Munich, Germany; 8 pages.

Watanable, E. et al., Three-Dimensional Digitizer (Neuronavigator); New Equipment for Computed Tomography-Guided Stereotaxic Surgery, Surgical Neurology, Jun. 1987, pp. 543-547, vol. 27, Issue 6, Elsevierinc; 5 pages.

Yoshimine, Kato A. et al., A frameless, armless navigational system for computer-assisted neurosurgery. Technical note, Journal of Neurosurgery, vol. 74, May 1991, pp. 845-849; 5 pages.

Zilles, C.B. et al., "A Constraint-Based God-object Method for Haptic Display", Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.

Hassfeld, S. et al., "Intraoperative Navigation Techniques Accuracy Tests and Clinical Report", Computer Assisted Radiology and Surgery (CARS'98), Tokyo, Jun. 1998, pp. 670-675,Elseview Science B.V.; 6 pages.

Ho, S.C. et al., "Robot Assisted Knee Surgery", IEEE Engineering in Medicine and Biology, May/Jun. 1995, pp. 292-300, vol. 14, No. 3; 9 pages.

Ho, S.C. et al., Force Control for Robotic Surgery, ICAR '95,1995, pp. 21-32, London, UK; 12 pages.

Hyosig, K. et al., Autonomous Suturing using Minimally Invasive Surgical Robots, Control Applications, Sep. 25-27, 2000. Proceedings of the 2000 IEEE International Conference on, 2000, pp. 742-747, IEEE, Anchorage, AK, USA; 6 pages.

Hyosig, K. et al., EndoBot A Robotic Assistant in Minimally Invasive Surgeries, Robotics and Automation, 2001. Proceedings 2001 ICRA. IEEE International Conference on, Seoul, KR, 2001, pp. 2031-2036, vol. 2, IEEE, Troy, NY, USA; 6 pages.

International Search Report for Application No. PCT/US2014/024269 dated Oct. 17, 2014, 6 pages.

International Search Report for Application No. PCT/US2016/069152 dated Apr. 6, 2017, 2 pages.

Jakopec, M. et al., The first clinical application of a "hands-on" robotic knee surgery system, Computer Aided Surgery , 2001, pp. 329-339, vol. 6, Issue 6, Wiley-Liss, Inc.; 11 pages.

Jaramaz, B. et al., Range of Motion After Total Hip Arthroplasty Experimental Verification of the Analytical Simulator, CVRMed—MRCAS'97, Lecture Notes in Computer Science, Feb. 20, 1997, pp. 573-582, vol. 1205,Springer Berlin Heidelberg, Pittsburgh, PA, USA; 14 pages.

Kazanzides, P. et al., Architecture of a Surgical Robot, Systems, Man and Cybernetics, 1992., IEEE International Conference on, Oct. 18-21, 1992, pp. 1624-1629, vol. 2, IEEE,Chicago, IL, USA; 6 pages.

Khadem, R. et al., Comparative Tracking Error Analysis of Five Different Optical Tracking Systems, Computer Aided Surgery, 2000, pp. 98-107, vol. 5, Stanford, CA,USA; 10 pages.

Kienzle, III, T.C. et al., Total Knee Replacement Computer-assisted surgical system uses a calibrated robot, Engineering in Medicine and Biology, May 1995, pp. 301-306, vol. 14, Issue 3,IEEE; 35 pages.

Kienzle, T.C. et al., "An Integrated CAD-Robotics System for Total Knee Replacement Surgery", Systems, Man and Cybernetics, 1992., IEEE International Conference on, Oct. 18-21, 1992, pp. 1609-1614, vol. 2,IEEE, Chicago, IL, USA; 6 pages.

Koseki, Y. et al., Robotic assist for MR-guided surgery using leverage and parallelepiped mechanism, Medical Image Computing and Computer-Assisted Intervention—MICCAI 2000, Lecture Notes in Computer Science, 2000, pp. 940-948, vol. 1935, Springer Berlin Heidelberg; 9 pages.

Lavallee, S. et al., Computer Assisted Spine Surgery a technique for accurate transpedicular screw fixation using CT data and a 3-D optical localizer, Journal of Image Guided Surgery, 1995, pp. 65-73; 9 pages.

Lea, J.T. et al., Registration and immobilization in robot-assisted surgery, Journal of Image Guided Surgery, Computer Aided Surgery, 1995, vol. 1, No. 2, pp. 80-87; 11 pages.

Lea, J.T. Registration Graphs a Language for Modeling and Analyzing Registration in Image-Guided Surgery, Dec. 1998, Evanston, Illinois, US; 49 pages.

Leitner, F. et al., Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.

Levison, T.J et al., Surgical Navigation forTHR a Report on Clinical Trial Utilizing HipNav, MICCAI 2000, LNCS 1935, pp. 1185-1187, 2000, Springer-Verlag Berlin Heidelberg; 3 pages.

Louhisalmi, Y. et al., Development of a Robotic Surgical Assistant, 1994, pp. 1043-1044, IEEE, Linnanmaa, Oulu, FI; 2 pages.

Machine-Assisted English language translation for WO 0021450 A1 extracted www.espacenet.com on Jul. 3, 2014; 28 pages.

Machine-Assisted English language translation for WO 0059397 A1 extracted www.espacenet.com Jul. 3, 2014; 33 pages.

Machine-Assisted English language translation for WO 02074500 extracted www.espacenet.com Apr. 30, 2014; 26 pages.

Matsen, F.A. et al., Robotic Assistance in Orthopaedic Surgery a Proof of Principle Using Distal Femoral Arthroplasty, Clinical Orthopaedic Related Research, Nov. 1993, pp. 178-186, vol. 296; 9pages.

Meng, C. et al., "Remote surgery case robot-assisted teleneurosurgery", Robotics and Automation, 2004. Proceedings. ICRA '04. 2004 IEEE International Conference on, Apr. 26-May 1, 2004, pp. 819-823, vol. 1, IEEE,New Orleans, LA, USA; 5 pages.

Moctezuma, J. L. et al., "A Computer and Robotic Aided Surgery System for Accomplishing Osteotomies", First International Symposium onMedical Robotics and Computer Assisted Surgery, Sep. 22-24, 1994, Piltsburgh, Pennsylvania, US; 6 pages.

Nolte, L.P. et al., A Novel Approach to Computer Assisted Spine Surgery, Proc. First International Symposium on Medical Robotics and Computer Assisted Surgery, Pittsburgh, 1994, pp. 323-328; 7 pages.

O'Toole, R.V. et al., Biomechanics for Preoperative Planning and Surgical Simulations in Orthopaedics, Computers in Biology and Medicine, Mar. 1995, pp. 183-191, vol. 25, Issue 2; 8 pages.

Orto Maquet and Caspar: An Automated Cell for Prosthesis Surgery, Robotics World, Sep./Oct. 1999, pp. 30-31, Circular No. 87 on Reader Reply Card; 2 pages.

Park, Shinsuk, "Safety Strategies for Human-Robot Interaction in Surgical Environment," SICE-ICASE, 2006. International Joint Conference, Oct. 18-21, 2006, pp. 1769-1773, IEEE, Bexco, Busan, SK; 5 pages.

Paul, H.A. et al., A Surgical Robot for Total Hip Replacement Surgery, International Conference on Robotics and Automation, 1992, pp. 606-611, IEEE,Nice, FR; 6 pages.

Paul, H.A. et al., "Development of a Surgical Robot for Cementless Total Hip Arthroplasty", Clinical Orthopaedics and Related Research, Dec. 1992, pp. 57-66, No. 285, Sacramento, CA, USA; 10 pages.

(56) References Cited

OTHER PUBLICATIONS

Paul, H.A. et al., Robotic Execution of a Surgical Plan, Systems, Man and Cybernetics, 1992., IEEE International Conference on, Oct. 18-21, 1992,pp. 1621-1623, IEEE, Sacramento, California, US; 3 pages.

Preising, B. et al., A Literature Review Robots in Medicine, Engineering in Medicine and Biology Magazine, IEEE (vol. 10, Issue: 2), Jun. 1991, pp. 13-22, IEEE; 10 pages.

Quaid, A.E. et al., Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.

Raczkowsky, J. et al., Ein Robotersystem fur craniomaxillofaciale chirurgische Eingriffe (A robotic system for surgical procedures craniomaxillofaciale), with English language abstract, Computer Forsch. Entw., 1999, pp. 24-35, vol. 14,Springer-Verlag; 12 pages.

Rembold, U. et al., Surgical Robotics: An Introduction, Journal of Intelligent and Robotic Systems vol. 30, No. 1, pp. 1-28, 2001, Kluwer Academic Publishers; 28 pages.

Riviere, C.N. et al., "Modeling and Canceling Tremor in Human-Machine Interfaces", Engineering in Medicine and Biology Magazine, IEEE, vol. 15, Issue 3, May/Jun. 1996, pp. 29-36, IEEE; 8 pages.

Rohling, R. et al., Comparison of Relative Accuracy Between a Mechanical and an Optical Position Tracker for Image-Guided Neurosurgery, Journal of Image Guided Surgery, 1995, pp. 30-34, vol. 1, No. 1; 4 pages.

Salisbury, J.K., Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.

Santos-Munne, Julio J. et al., A Stereotactic/Robotic System for Pedicle Screw Placement, Interactive Technology and the New Paradigm for Healthcare, (Proceedings of theMedicine Meets Virtual Reality III Conference, San Diego, 1995), pp. 326-333, IOS Press and Ohmsha; 8 pages.

Schmidt, T. et al., EasyGuide Neuro, A New System for Image-Guided Planning, Simulation and Navigation in Neurosurgery, Biomedical Engineering, vol. 40, Supplement 1, 1995, pp. 233-234, Hamburg, DE; 2 pages, and partial English language translation of EasyGuide Neuro, A New System for Image-Guided Planning, Simulation and Navigation in Neurosurgery, 1 page.

Seibold, U. et al. ."Prototype of Instrument for Minimally Invasive Surgery with 6-Axis Force Sensing Capability", Robotics and Automation,2005. ICRA 2005. Proceedings of the 2005 IEEE International Conference on, Apr. 18-22, 2005, pp. 498-503, IEEE, Barcelona, Spain; 6 pages.

Siebert W. et al., "Technique and first clinical results of robot-assisted total knee replacement", The Knee, Sep. 2002, pp. 173-180, vol. 9, Issue 3, Elsevier B.V.; 8 pages.

Sim, C. et al., Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.

Simon, D.A. et al., Accuracy validation in image-guided orthopaedic surgery, In Medical Robotics and Computer Assisted Surgery, 1995, pp. 185-192, Wiley; 8 pages.

Spencer, E.H., The ROBODOC Clinical Trial a Robotic Assistant for Total Hip Arthroplasty, Orthopaedic Nursing, Jan.-Feb. 1996, pp. 9-14, vol. 15, Issue 1; 6 pages.

Spetzger, U. et al., Frameless Neuronavigation in Modern Neurosurgery, Minimally Invasive Neurosurgery, Dec. 1995, pp. 163-166, vol. 38; 4 pages.

Taylor, R. et al., A Steady-Hand Robotic System for Microsurgical Augementation, MICCAI99: the Second International Conference on Medical ImageComputing and Computer-Assisted Intervention, Cambridge, England, Sep. 19-22, 1999. MICCAI99 Submission #1361999, pp. 1031-1041, Springer-Verlag Berlin Heidelberg; 11 pages.

Taylor, R.H et al. "An Image-directed Robotic System for Hip Replacement Surgery", Oct. 1990, pp. 111-116, vol. 3, No. 5; 7 pages.

\* cited by examiner

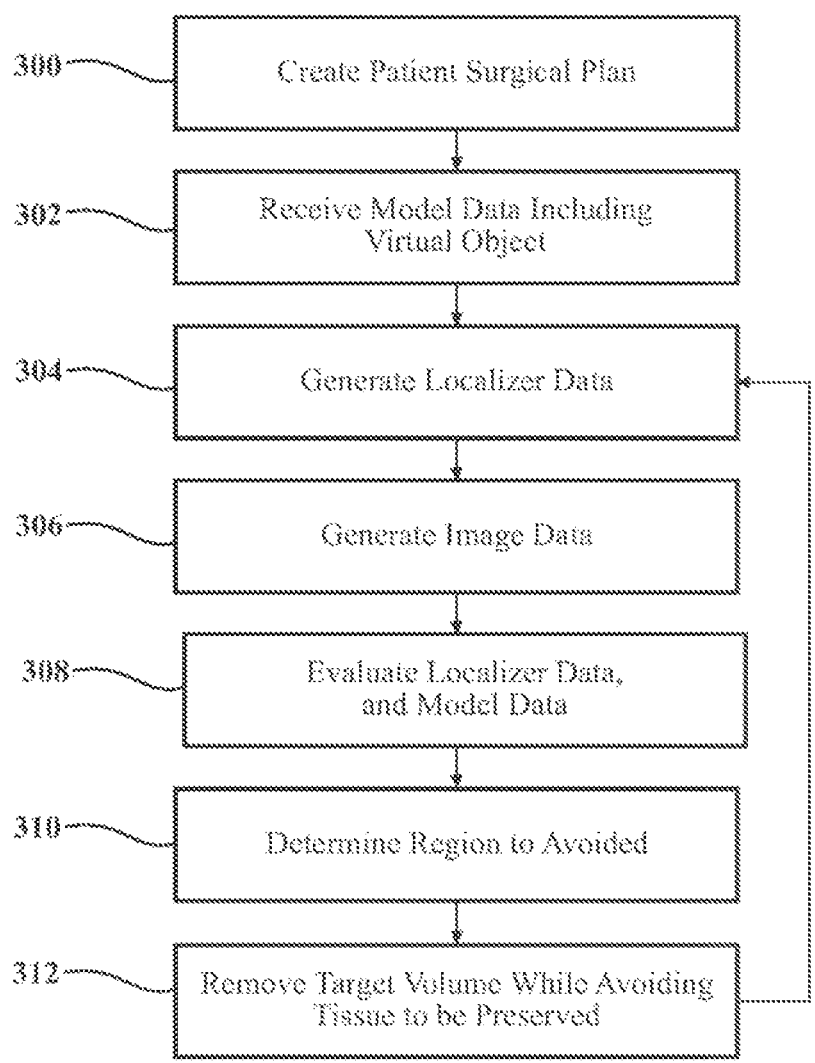

MERGING LOCALIZATION AND VISION DATA FOR ROBOTIC CONTROL

CROSS-REFERENCE TO RELATED APPLICATIONS

This application is a continuation of U.S. Non-provisional patent application Ser. No. 16/880,335, filed May 21, 2020, which is a continuation of U.S. Non-provisional patent application Ser. No. 15/393,876, filed Dec. 29, 2016, now U.S. Pat. No. 10,667,868, which claims priority to and the benefit of U.S. Provisional Pat. App. No. 62/273,543, filed Dec. 31, 2015, the contents and disclosure of each of the above-referenced applications being hereby incorporated by reference in their entirety.

TECHNICAL FIELD

The present disclosure relates generally to techniques for merging localization and vision data for robotic control.

BACKGROUND

Navigation systems assist users in precisely locating objects. For instance, navigation systems are used in industrial, aerospace, and medical applications. In the medical field, navigation systems assist surgeons in precisely placing surgical instruments relative to a target site in a patient. The target site usually requires some form of treatment, such as tissue removal. In some cases, the target site is defined in the navigation system using a virtual object, such as a 3-D model. A representation of the virtual object can be displayed to the user during surgery to assist the user in visualizing placement of a treatment end of the instrument relative to the target site. For instance, the target site may be associated with a bone of the patient and the virtual object may define a volume of the bone to be removed by the treatment end of the instrument.

Conventional navigation systems employ a localizer that cooperates with trackers to provide position and/or orientation data associated with the instrument and the target site, e.g., the volume of the bone to be removed. The localizer is usually placed so that it has a field of view of the trackers. The trackers are fixed to the instrument and to the patient to move in concert with the instrument and the patient. The tracker attached to the patient is attached to the bone being treated thereby maintaining a rigid relationship with respect to the target site owing to the rigid nature of the bone. By using separate trackers on the instrument and the patient, the treatment end of the instrument can be precisely positioned to stay within the target site.

Often, the target site is located adjacent to sensitive anatomical structures, such as soft tissue, that should be avoided during surgery. These sensitive anatomical structures are difficult to track using conventional trackers, as these sensitive anatomical structures can shift relative to the trackers due to their elastic and/or flexible nature. Just as often, retractors or other tools are located near the target site that should also be avoided during the surgery. The retractors or other tools could be tracked in the same manner as the instrument being used for treating the patient, but adding trackers to the retractors and other tools can substantially increase costs and complexity in the navigation system, particularly by increasing the number of objects to be tracked by the navigation system. As a result, in current surgical procedures, avoidance is sometimes the responsibility of the user, so extreme care must be taken by the user to avoid sensitive anatomical structures and untracked tools that may be near the target site.

Thus, there is a need in the art for navigation systems and methods that address the identification of sensitive anatomical structures and/or other structures that are to be avoided during surgery.

SUMMARY

In one aspect, a surgical system is provided, with the surgical system comprising: a localizer configured to generate localizer data associated with a bone; a vision device configured to generate, in a coordinate system of the vision device, image data associated with the bone and an environment of the bone within a field-of-view of the vision device; a robotic manipulator configured to support and move a surgical instrument; and one or more controllers being configured to: associate a virtual object with the bone; determine a position and orientation of the virtual object based on the localizer data; merge the image data and the localizer data associated with the bone into a common coordinate system; and control the robotic manipulator based on an output of merging the image data and the localizer data.

In another aspect, a method of operating a surgical system is provided, the surgical system comprising a localizer configured to generate localizer data associated with a bone, a vision device configured to generate, in a coordinate system of the vision device, image data associated with the bone and an environment of the bone within a field-of-view of the vision device, a robotic manipulator configured to support and move a surgical instrument, and one or more controllers, the method comprising: associating, with the one or more controllers, a virtual object with the bone; determining, with the one or more controllers, a position and orientation of the virtual object based on the localizer data; merging, with the one or more controllers, the image data and the localizer data associated with the bone into a common coordinate system; and controlling, with the one or more controllers, the robotic manipulator based on an output of merging the image data and the localizer data.

These systems and methods provide several advantages. For instance, by capturing both localizer data using the localizer and image data using the vision device, the navigation computer is able to identify the region to be avoided that is located outside of the object. As a result, these systems and methods, in some embodiments, provide for accurate placement of surgical instruments to avoid collisions with other objects, tools, or sensitive anatomical structures that are otherwise difficult to track and that may not be outfitted with separate trackers.

BRIEF DESCRIPTION OF THE DRAWINGS

Advantages will be readily appreciated as the same becomes better understood by reference to the following detailed description when considered in connection with the accompanying drawings.

FIG. 5 is a flow chart of steps carried out by a method of treating the patient.

DETAILED DESCRIPTION

Figure 1:
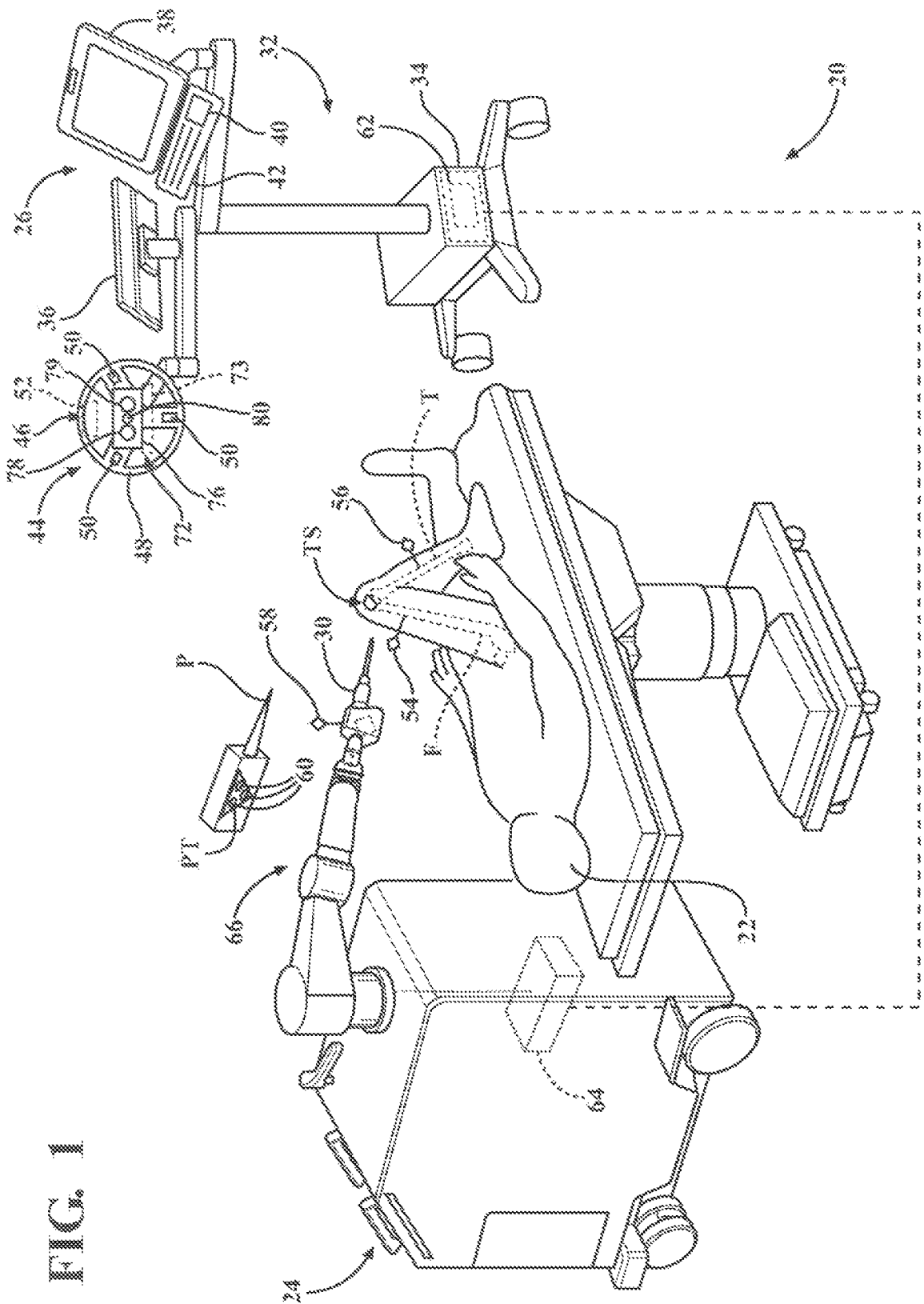
FIG. 1 is a perspective view of a robotic surgical system comprising a localizer and a vision device.

As shown in FIG. 1, a system 20 for treating a patient 22 is illustrated. The system 20 is shown in a surgical setting such as an operating room of a medical facility. In the embodiment shown, the system 20 comprises a machining station 24 and a guidance station 26. The guidance station 26 is set up to track movement of various objects in the operating room. Such objects include, for example, a surgical instrument 30, a femur F of a patient, and a tibia T of the patient. The guidance station 26 tracks these objects for purposes of displaying their relative positions and orientations to a user and, in some cases, for purposes of controlling or constraining movement of the surgical instrument 30 relative to target sites. The surgical instrument 30 is shown as part of the machining station 24. However, in other embodiments, the surgical instrument 30 is manually held and moved by the user.

The target sites to be treated by the surgical instrument 30 are defined by virtual objects. In the embodiment shown, a femur target site TS is shown, which is associated with the femur F. Of course, several other target sites, such as a target site for the tibia T, are also possible, with each being defined by its own separate virtual object. The virtual objects representing the target sites are pre-operatively set by the user and/or automatically generated to define volumes of material to be treated, trajectories for the surgical instrument 30, planes to be cut by the surgical instrument 30, bores to be drilled, and the like. In the embodiment shown, a virtual object VB (see FIG. 4) defines the volume of material to be removed from the femur F. In some cases, the virtual objects are set or re-set intraoperatively, i.e., during the surgical procedure. It should be appreciated that although the description set forth herein relates to orthopedic surgical procedures, the systems and methods described herein are likewise suitable for any type of surgical procedure.

The guidance station 26 includes a navigation cart assembly 32 that houses a navigation computer 34. A navigation interface is in operative communication with the navigation computer 34. The navigation interface includes a first display 36 adapted to be situated outside of the sterile field and a second display 38 adapted to be situated inside the sterile field. The displays 36, 38 are adjustably mounted to the navigation cart assembly 32. First and second input devices 40, 42 such as a keyboard and mouse can be used to input information into the navigation computer 34 or otherwise select/control certain aspects of the navigation computer 34. Other input devices are contemplated including a touch screen (not shown) or voice-activation.

A localizer 44 communicates with the navigation computer 34. In the embodiment shown, the localizer 44 is an optical localizer and includes a localizer camera unit 46. The localizer camera unit 46 has an outer casing 48 that houses one or more optical position sensors 50. In some embodiments at least two optical sensors 50 are employed, preferably three, four, or more. The optical sensors 50 may be three separate charge-coupled devices (CCD). In one embodiment three, one-dimensional CCDs are employed. It should be appreciated that in other embodiments, separate localizer camera units, each with a separate CCD, or two or more CCDs, could also be arranged around the operating room. The CCDs detect infrared signals. Additionally, the localizer 44 may employ different modalities and may be an electromagnetic localizer, RF localizer, ultrasound localizer, or any other conventional localizer capable of tracking objects.

The localizer camera unit 46 is mounted to an adjustable arm to position the optical sensors 50 with a field of view of the below discussed trackers that, ideally, is free from obstructions. In some embodiments the localizer camera unit 46 is adjustable in at least one degree of freedom by rotating about a rotational joint. In other embodiments, the localizer camera unit 46 is adjustable about two or more degrees of freedom.

The localizer camera unit 46 includes a localizer camera controller 52 in communication with the optical sensors 50 to receive signals from the optical sensors 50. The localizer camera controller 52 communicates with the navigation computer 34 through either a wired or wireless connection (not shown). One such connection may be an IEEE 1394 interface, which is a serial bus interface standard for high-speed communications and isochronous real-time data transfer. The connections could also use a company specific protocol. In other embodiments, the optical sensors 50 communicate directly with the navigation computer 34.

Position and orientation signals and/or data are transmitted to the navigation computer 34 for purposes of tracking objects. The navigation cart assembly 32, displays 36, 38, and localizer camera unit 46 may be like those described in U.S. Pat. No. 7,725,162 to Malackowski, et al. issued on May 25, 2010, entitled "Surgery System," hereby incorporated by reference.

Navigation computer 34 has the displays 36, 38, central processing unit (CPU) and/or other processors 62, memory (not shown), and storage (not shown) necessary for carrying out the functions described herein. The navigation computer 34 is loaded with software as described below. The software converts the signals received from the localizer camera unit 46 into localizer data representative of the position and orientation of the objects being tracked.

Guidance station 26 is operable with a plurality of tracking devices 54, 56, 58, also referred to herein as trackers. In the illustrated embodiment, one tracker is 54 is firmly affixed to the femur F of the patient and another tracker 56 is firmly affixed to the tibia T of the patient. Trackers 54, 56 are firmly affixed to sections of bone. Trackers 54, 56 may be attached to the femur F and tibia T in the manner shown in U.S. Pat. No. 7,725,162, hereby incorporated by references. Trackers 54, 56 could also be mounted like those shown in U.S. Patent Application Publication No. 2014/0200621, filed on Jan. 16, 2014, entitled, "Navigation Systems and Methods for Indicating and Reducing Line-of-Sight Errors," hereby incorporated by reference herein. In yet further embodiments, the trackers 54, 56 could be mounted to other tissues of the anatomy.

An instrument tracker 58 is firmly attached to the surgical instrument 30. The instrument tracker 58 may be integrated into the surgical instrument 30 during manufacture or may be separately mounted to the surgical instrument 30 in preparation for surgical procedures. A treatment end of the surgical instrument 30, which is being tracked by virtue of the instrument tracker 58, may be a rotating bur, electrical ablation device, or the like.

The trackers 54, 56, 58 can be battery powered with an internal battery or may have leads to receive power through the navigation computer 34, which, like the localizer camera unit 46, preferably receives external power.

In the embodiment shown, the surgical instrument 30 is attached to a manipulator 66 of the machining station 24. The manipulator 66 may also be referred to as a robotic device or a robotic arm. Such an arrangement is shown in U.S. Pat. No. 9,119,655, entitled, "Surgical Manipulator Capable of Controlling a Surgical Instrument in Multiple Modes," the disclosure of which is hereby incorporated by reference. It should be appreciated that in other embodiments, the surgical instrument 30 is manually manipulated without any robotic constraint on its position and/or orientation. The surgical instrument 30 may be any surgical instrument (also referred to as a tool) that is useful in performing medical/surgical procedures. The surgical instrument 30 may be a burring instrument, an electrosurgical instrument, an ultrasonic instrument, a reamer, an impactor, a sagittal saw, or other instrument. In some embodiments, multiple surgical instruments are employed to treat the patient, with each being separately tracked by the localizer 44.

The optical sensors 50 of the localizer 44 receive light signals from the trackers 54, 56, 58. In the illustrated embodiment, the trackers 54, 56, 58 are active trackers. In this embodiment, each tracker 54, 56, 58 has at least three active tracking elements or markers for transmitting light signals to the optical sensors 50. The active markers can be, for example, light emitting diodes or LEDs 60 transmitting light, such as infrared light. The optical sensors 50 preferably have sampling rates of 100 Hz or more, more preferably 300 Hz or more, and most preferably 500 Hz or more. In some embodiments, the optical sensors 50 have sampling rates of 8000 Hz. The sampling rate is the rate at which the optical sensors 50 receive light signals from sequentially fired LEDs 60. In some embodiments, the light signals from the LEDs 60 are fired at different rates for each tracker 54, 56, 58.

Figure 2:
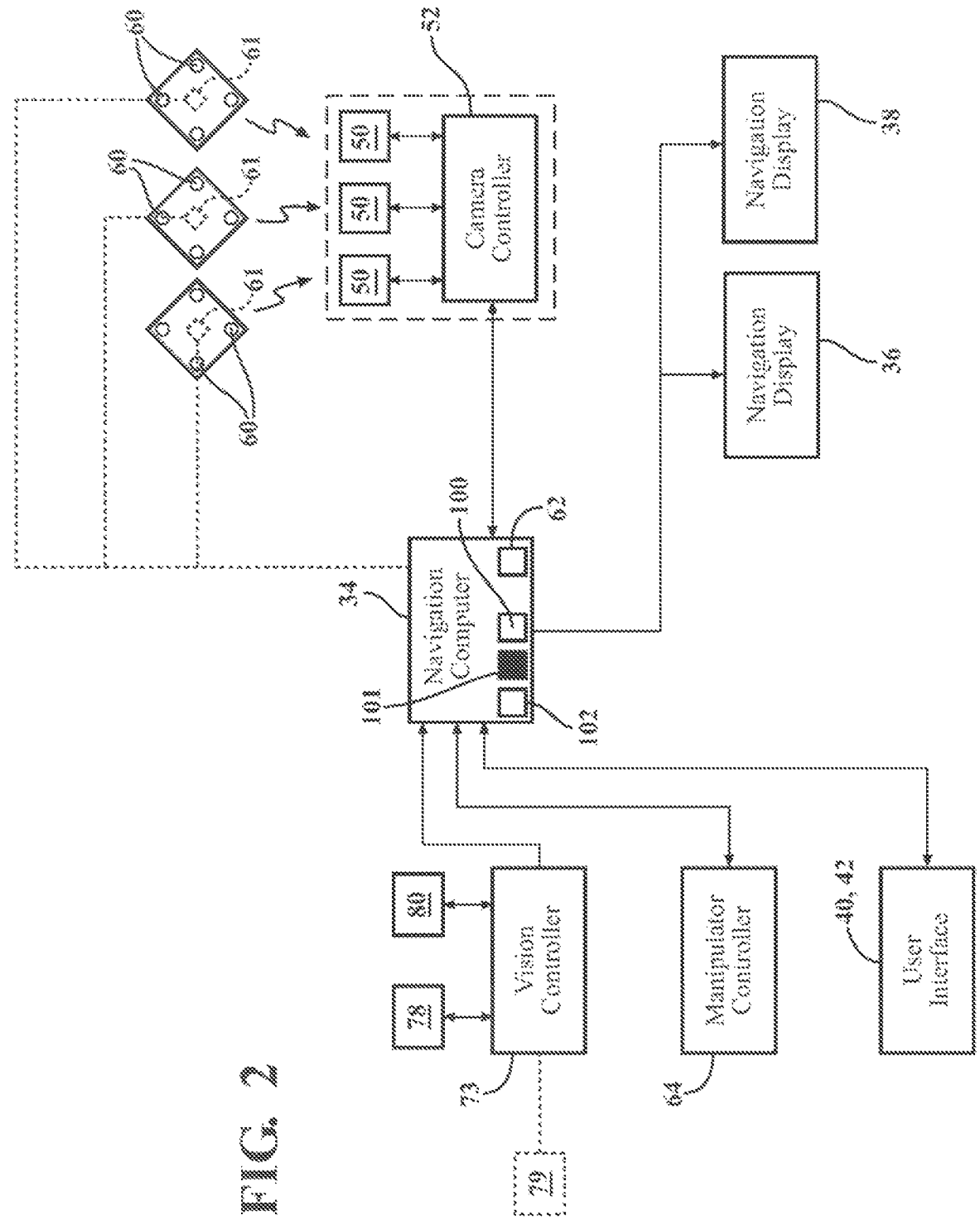
FIG. 2 is a schematic view of a control system for controlling the robotic surgical system.

Referring to FIG. 2, each of the LEDs 60 are connected to a tracker controller 61 located in a housing of the associated tracker 54, 56, 58 that transmits/receives data to/from the navigation computer 34. In one embodiment, the tracker controllers 61 transmit data on the order of several Megabytes/second through wired connections with the navigation computer 34. In other embodiments, a wireless connection may be used. In these embodiments, the navigation computer 34 has a transceiver (not shown) to receive data from the tracker controller.

In other embodiments, the trackers 54, 56, 58 may have passive markers (not shown), such as reflectors that reflect light emitted from the localizer camera unit 46. The reflected light is then received by the optical sensors 50. Active and passive arrangements are well known in the art.

In some embodiments, the trackers 54, 56, 58 also include a gyroscope sensor and accelerometer, such as the trackers shown in U.S. Pat. No. 9,008,757 to Wu, issued on Apr. 14, 2015, entitled "Navigation System Including Optical and Non-Optical Sensors," hereby incorporated by reference.

The navigation computer 34 includes the navigation processor 62. It should be understood that the navigation processor 62 could include one or more processors to control operation of the navigation computer 34. The processors can be any type of microprocessor or multi-processor system. The term processor is not intended to limit the scope of any embodiment to a single processor.

The localizer camera unit 46 receives optical signals from the LEDs 60 of the trackers 54, 56, 58 and outputs to the navigation processor 62 signals relating to the position of the LEDs 60 of the trackers 54, 56, 58 relative to the localizer 44. Based on the received optical (and non-optical signals in some embodiments), navigation processor 62 generates data indicating the relative positions and orientations of the trackers 54, 56, 58 relative to the localizer 44, such as through known triangulation methods. In some embodiments, the data is generated by the localizer camera controller 52 and then transmitted to the navigation computer 34.

Prior to the start of the surgical procedure, additional data are loaded into the navigation processor 62. Based on the position and orientation of the trackers 54, 56, 58 and the previously loaded data, navigation processor 62 determines the position of the treatment end of the surgical instrument 30 (e.g., the centroid of a surgical bur) and the orientation of the surgical instrument 30 relative to the target sites against which the treatment end is to be applied, such as the femur target site TS. In some embodiments, navigation processor 62 forwards these data to a manipulator controller 64. The manipulator controller 64 can then use the data to control the manipulator 66 as described in U.S. Pat. No. 9,119,655, entitled, "Surgical Manipulator Capable of Controlling a Surgical Instrument in Multiple Modes," the disclosure of which is hereby incorporated by reference. In one embodiment, the manipulator 66 is controlled with respect to the virtual objects set by the surgeon. In the embodiment described herein, the virtual object VB defines the volume of material of the femur F to be removed by the surgical instrument 30. Thus, the virtual object VB provides a virtual boundary for the treatment end of the surgical instrument 30 to stay within (i.e., for a separate virtual object associated with the treatment end of the surgical instrument to stay within).

The navigation processor 62 also generates image signals that indicate the relative position of the treatment end to the target sites. These image signals are applied to the displays 36, 38. Displays 36, 38, based on these signals, generate images that allow the surgeon and staff to virtually view the relative position of the treatment end to the target sites. In most cases, the images illustrate the treatment end with respect to one target site at a time. For instance, in a surgical procedure in which the femur F and the tibia T are both being treated, the femur target site TS and the relative position of the treatment end of the surgical instrument 30 to the femur target site TS may be visually represented while material is being removed from the femur F. Likewise, when the user is finished removing material from the femur F and is ready to remove material from the tibia T, the display 36, 38 may only illustrate placement of the treatment end of the surgical instrument 30 with respect to the target site associated with the tibia T.

Figure 3:
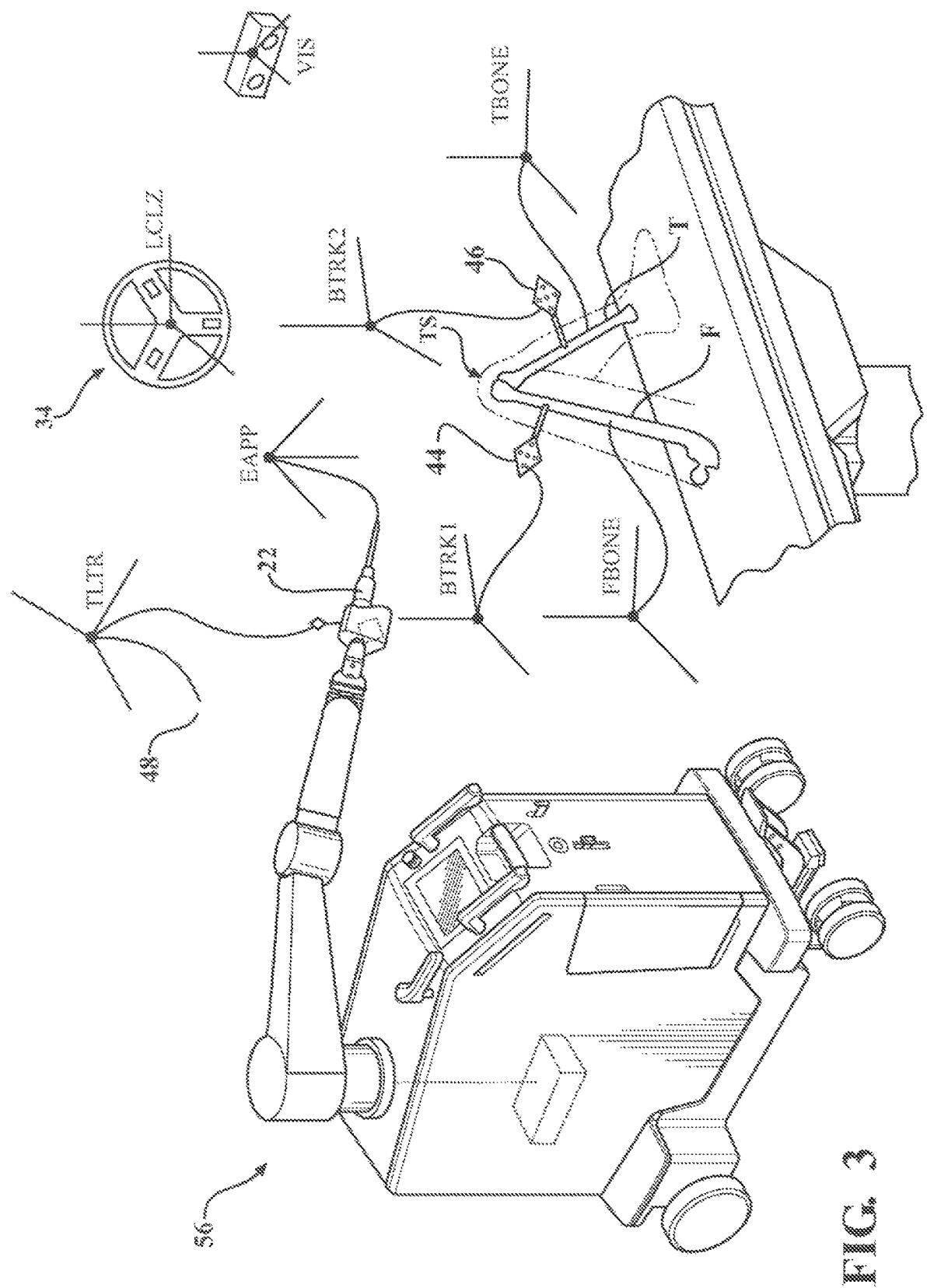
FIG. 3 is a perspective view of coordinate systems used in the robotic surgical system.

Referring to FIG. 3, tracking of objects is generally conducted with reference to a localizer coordinate system LCLZ. The localizer coordinate system LCLZ has an origin and an orientation (a set of x, y, and z axes). During the procedure one goal is to keep the localizer coordinate system LCLZ in a known position. An accelerometer (not shown) mounted to the localizer camera unit 46 may be used to track sudden or unexpected movement of the localizer coordinate system LCLZ, as may occur when the localizer camera unit 46 is inadvertently bumped by surgical personnel.

Each tracker 54, 56, 58, and object being tracked also has its own coordinate system separate from the localizer coordinate system LCLZ. For instance, the trackers 54, 56, 58 have bone tracker coordinate system BTRK1, bone tracker coordinate system BTRK2, and instrument tracker coordinate system TLTR.

In the embodiment shown, the guidance station 26 monitors the positions of the femur F and tibia T of the patient by monitoring the position of bone trackers 54, 56 firmly attached to bone. Femur coordinate system is FBONE and tibia coordinate system is TBONE, which are the coordinate systems of the bones to which the bone trackers 54, 56 are firmly attached.

Prior to the start of the procedure, pre-operative images of the anatomy of interest are generated, such as pre-operative images of the femur F and tibia T (or of other tissues or structures in other embodiments). These images may be based on MRI scans, radiological scans or computed tomography (CT) scans of the patient's anatomy. These images are used to develop virtual models of anatomy of interest, such as virtual models of the femur F and tibia T and/or other anatomy to be treated by the surgical instrument 30. Often the virtual models are 3-D models that comprise data representing the entire anatomy being treated or at least a portion of the anatomy to be treated and data representing the virtual objects that define the target sites. In the embodiment shown, a virtual model VM of the femur is a 3-D model comprising model data that represents a portion of the femur F and the virtual object VB (see FIG. 4). The virtual object VB defines the target site TS and the volume of material to be removed from the femur F during the surgical procedure. The virtual objects may be defined within the virtual models and may be represented as mesh surfaces, constructive solid geometries (CSG), voxels, or using other virtual object representation techniques.

The pre-operative images and/or the virtual models are mapped to the femur coordinate system FBONE and tibia coordinate system TBONE using well known methods in the art. These pre-operative images and/or virtual models are fixed in the femur coordinate system FBONE and tibia coordinate system TBONE. As an alternative to taking pre-operative images, plans for treatment can be developed in the operating room from kinematic studies, bone tracing, and other methods. These same methods could also be used to generate the 3-D virtual models previously described.

During an initial phase of the procedure described herein, the bone trackers 54, 56 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIG. 1), such as disclosed in U.S. Pat. No. 7,725,162 to Malackowski, et al., hereby incorporated by reference, having its own tracker PT (see FIG. 1), may be used to register the femur coordinate system FBONE and tibia coordinate system TBONE to the bone tracker coordinate systems BTRK1 and BTRK2, respectively. Given the fixed relationship between the bones and their trackers 54, 56, positions and orientations of the femur F and tibia T in the femur coordinate system FBONE and tibia coordinate system TB ONE can be transformed to the bone tracker coordinate systems BTRK1 and BTRK2 so the localizer camera unit 46 is able to track the femur F and tibia T by tracking the trackers 54, 56. These pose-describing data are stored in memory integral with both the manipulator controller 64 and the navigation processor 62.

The treatment end of the surgical instrument 30 (also referred to as a distal end of an energy applicator) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with manipulator controller 64 and navigation processor 62.

Referring to FIG. 2, a localization engine 100 is a software module that can be considered part of the navigation computer 34. Components of the localization engine 100 run on navigation processor 62. The localization engine 100 may run on the manipulator controller 64 and/or the navigation processor 62.

Localization engine 100 receives as inputs the optically-based signals from the localizer camera controller 52 and, in some embodiments, the non-optically based signals from the tracker controller (not shown). Based on these signals, localization engine 100 determines the pose of the bone tracker coordinate systems BTRK1 and BTRK2 in the localizer coordinate system LCLZ. Based on the same signals received for the instrument tracker 58, the localization engine 100 determines the pose of the instrument tracker coordinate system TLTR in the localizer coordinate system LCLZ.

The localization engine 100 forwards the signals representative of the poses of trackers 54, 56, 58 to a coordinate transformer 102. Coordinate transformer 102 is a software module that runs on navigation processor 62. Coordinate transformer 102 references the data that defines the relationship between the pre-operative images and/or the virtual models of the patient and the bone trackers 54, 56. Coordinate transformer 102 also stores the data indicating the pose of the treatment end of the surgical instrument 30 relative to the instrument tracker 58. Coordinate transformer 102 also references the data that defines the virtual objects, if separate from the virtual models.

During the procedure, the coordinate transformer 102 receives the data indicating the relative poses of the trackers 54, 56, 58 to the localizer 44. Based on these data and the previously loaded data, the coordinate transformer 102 generates data indicating the relative position and orientation of both the coordinate system EAPP, and the bone coordinate systems, FBONE, TBONE to the localizer coordinate system LCLZ.

As a result, coordinate transformer 102 generates data indicating the position and orientation of the treatment end of the surgical instrument 30 relative to the target sites against which the treatment end is applied. Image signals representative of these data are forwarded to displays 36, 38 enabling the surgeon and staff to view this information. In certain embodiments, other signals representative of these data can be forwarded to the manipulator controller 64 to guide the manipulator 66 and corresponding movement of the surgical instrument 30. Thus, this data also indicates a virtual location of the treatment end of the surgical instrument 30, which may also be modeled as a separate virtual object, with respect to the virtual models and the virtual objects.

Referring back to FIG. 1, the guidance station 26 further includes a vision device 72. In the embodiment shown, the vision device is mounted to the localizer camera unit 46. In other embodiments, the vision device 72 may be mounted on a separate adjustable arm to position the vision device 72 separately from the localizer camera unit 46. The vision device 72 is preferably placed with a field of view of the target sites free from obstructions. The vision device 72 has a vision controller 73 in operative communication with the navigation computer 34. The vision device 72 may also be referred to as an imaging device or a digital imaging device capable of capturing 3-D images in real-time. One example of a suitable vision device is the commercially available Kinect SDK or similar Kinect model, sold by Microsoft Corporation. In other embodiments, the vision device 72 may comprise a laser array or a stereo camera system.

The vision device 72 has an outer housing 76 that supports one or more image sensors 78, 79. One of the image sensors may be a depth image sensor 78 used to identify a depth image, while the other image sensor may be a color image sensor 79 used to generate color images. Both image sensors 78, 79 may be in the form of CMOS sensors or other suitable sensors. Additionally, a light source 80 is supported in the housing 76 to generate and transmit light that is reflected back by surfaces in the field of view of the depth image sensor 78.

The sensors 78, 79 and the light source 80 communicate with the vision controller 73 to determine the distances of the surfaces in the field of view with respect to a vision coordinate system VIS (see FIG. 3). In one embodiment the light source 80 emits infrared light and the vision controller 73 determines the elapsed time required for the infrared light to reflect off the surfaces in the field of view and return to the depth image sensor 78. This process is repeated over a plurality of iterations to determine distances from the vision device 72 to surfaces in the field of view of the vision device 72 so that a point cloud 202 can be generated (see FIG. 4).

The navigation computer 34 communicates with the vision controller 73 to receive signals and/or data representative of the point cloud 202. Imaging software, comprising an image generator module, is loaded on the navigation computer 34 and run by the navigation processor 62 to create the point cloud 202 based on the field of view of the vision device 72. The point cloud 202 is created in the vision coordinate system VIS. The point cloud 202 is a set of image data points in the vision coordinate system VIS that correspond to the surfaces in the field of view of the vision device 72. These image data points are defined by x, y, z coordinates. The point cloud 202 can be saved or stored as an image data file.

It should be appreciated that by integrating the vision device 72 into the localizer camera unit 46, the vision coordinate system VIS can be easily registered to the localizer coordinate system LCLZ since the location of the image sensors 78, 79 relative to the optical sensors 50, and vice versa, is known and fixed. During manufacturing the vision device 72 can be calibrated to the localizer 44 to generate data with respect to the same coordinate system so that the vision coordinate system VIS does not need to be transformed to the localizer coordinate system LCLZ via the coordinate transformer 102.

In other embodiments, such as those in which the vision device 72 is separate from the localizer camera unit 46, the vision device 72 may have a tracker (not shown) rigidly mounted to the housing 76 to establish a relationship between the vision coordinate system VIS and the localizer coordinate system LCLZ. For instance, using preloaded data defining a relationship between the tracker's coordinate system and the vision coordinate system VIS, the coordinate transformer 102, based on the position of the tracker in the localizer coordinate system LCLZ, could transform the vision coordinate system VIS to the localizer coordinate system LCLZ.

Figure 4:
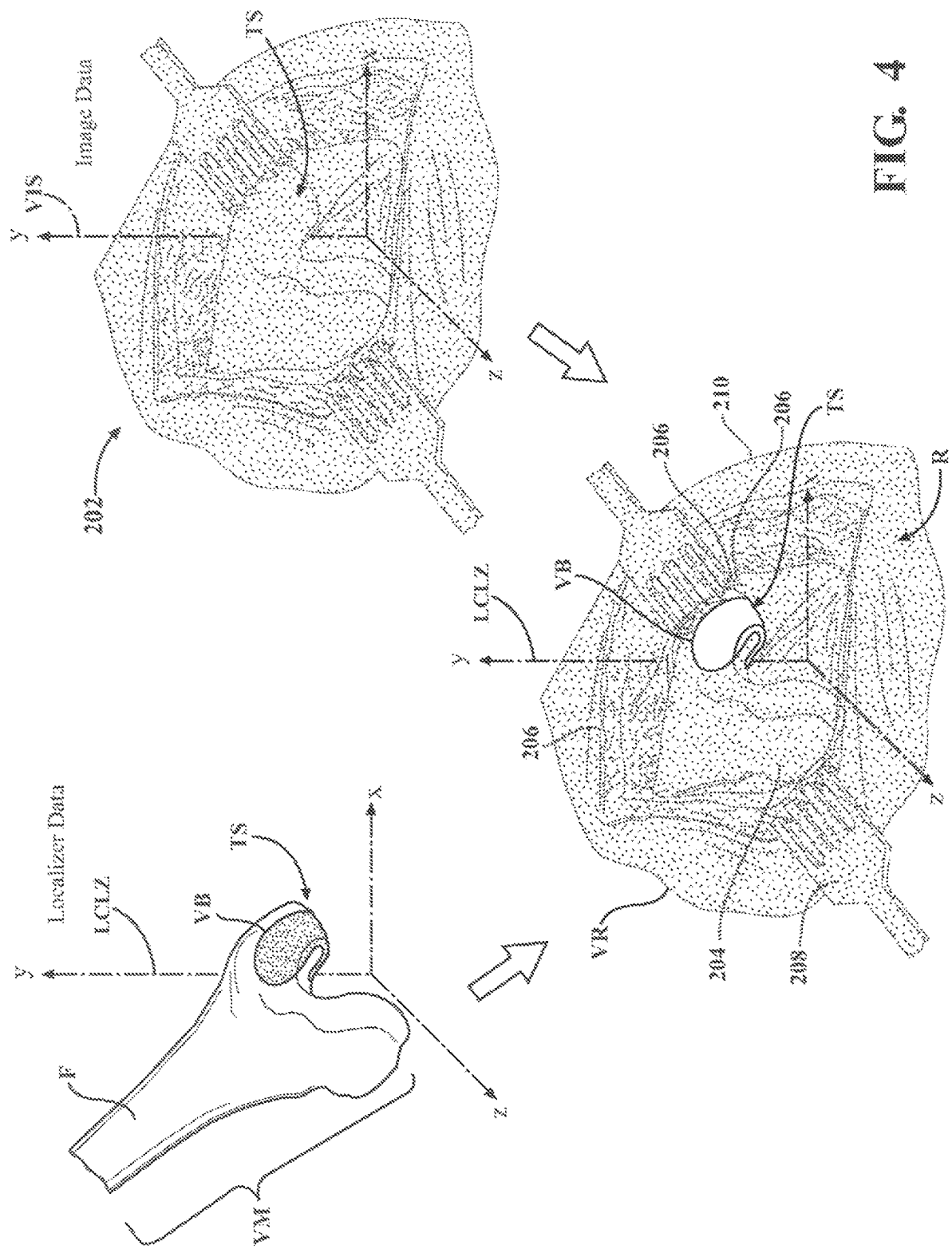
FIG. 4 is an illustration of image data from the vision device being combined with localizer data from the localizer to yield a virtual object defining a region to be avoided.

Referring to FIG. 4, the vision device 72 collects images of the target sites and the surfaces surrounding the target sites that are in the field of view of the vision device 72. In the embodiment shown, the vision device 72 collects images of the target site TS and the surfaces surrounding the target site TS that are in the field of view of the vision device 72. The navigation computer 34 cooperates with the vision controller 73 to create the point cloud 202 of the target site TS and the surfaces surrounding the target site TS, which defines image data associated with the target site TS and the surfaces surrounding the target site TS.

At the same time that the image data is being generated, the localizer data is also being generated. The navigation computer 34 cooperates with the localizer 44 to determine a position and orientation of the virtual models and the virtual objects defining the target sites in the localizer coordinate system LCLZ. In the embodiment shown, the navigation computer 34 cooperates with the localizer 44 to determine a position and orientation of the virtual model VM of the femur F and the position and orientation of the virtual object VB in the localizer coordinate system LCLZ. This localizer data comprises the model data defining the virtual model VM and the virtual object VB. In some cases, the model data includes data points in the form of a point cloud associated with the virtual model VM and a separate point cloud associated with the virtual object VB.

Still referring to FIG. 4, the navigation processor 62 runs a data merge module 101 (see FIG. 1), which is a software module that merges the localizer data and the image data to yield merged data (once the localizer data and the image data is located in, or transformed to, a common coordinate system). The merged data represents a second virtual object VR that defines a region R to be avoided during the surgery that is outside of the target site TS. This merging of data is illustrated by arrows in FIG. 4. In the embodiment shown, the merged data that represents the second virtual object VR may comprise: (1) data points 204 associated with bone that is to be avoided by the surgical instrument 30 that is outside of the target site TS; (2) data points 206 associated with exposed soft tissue that is to be avoided by the surgical instrument 30 that is outside of the target site TS; (3) data points 208 associated with retractors that are to be avoided by the surgical instrument 30; and (4) data points 210 associated with skin of the patient that is outside of the target site TS.

In some embodiments, like that shown in FIG. 4, the merged data comprises all data points in the point cloud 202 that have coordinates located outside of the virtual object VB after the localizer data and the image data are merged. In some cases, when a path for the treatment end of the surgical instrument 30 to reach the target site TS is not completely clear, such as when the target site TS is at least partially obstructed by soft tissue or other sensitive anatomical structures, defining all visible surfaces outside of the target site TS as part of the second virtual object VR can be particularly advantageous so that the surgical instrument 30 is able to avoid any sensitive anatomical structures, tools, etc., that are located outside of the target site TS.

The merged data that represents the second virtual object VR, and which defines the region R to be avoided, can be processed by the navigation processor 62 so that a representation thereof can be displayed to the user on the displays 38, 39 and the user can visualize a position and orientation of the surgical instrument 30 relative to the region R. In some cases, the data points that virtually define the region R to be avoided can be converted into a mesh surface, a constructive solid geometry (CSG), voxels, or other virtual object types using various virtual object representation techniques. Additionally, the navigation processor 62 may automatically limit the size of the second virtual object VR, and thus the extent of the region R, to a predefined distance from the target site TS, or the user may be able to manually refine the second virtual object VR, including defining an outer perimeter of the second virtual object VR.

It should be noted that the second virtual object VR may change in configuration (e.g., size, shape, position, etc.)

during the surgical procedure owing to the elastic and/or flexible nature of some of the tissues in the region R defined by the second virtual object VR. Additionally, the region R may change as retractors are adjusted, or as additional tools or equipment are brought into and out of the field of view of the vision device 72. In other words, the nature of the region R to be avoided is dynamic and may continuously change, but with the navigation techniques described herein, the second virtual object VR can be continuously updated (e.g., at a predefined frequency) with each new set of image data and localizer data so that the user is able to avoid the region R to be avoided during the surgical procedure regardless of changes to the region R.

The second virtual object VR that defines the region R to be avoided can also be transmitted to the manipulator controller 64 and treated as a "no-fly" zone in which the treatment end of the surgical instrument 30 is prevented from entering. As a result, when the manipulator 66 operates in an autonomous mode, the manipulator 66 is able to control positioning of the surgical instrument 30 to avoid the region R and thereby avoid sensitive anatomical structures, such as soft tissue and bone to be preserved, and tools, such as retractors, suction tubes, and the like, located near the target site TS.

Referring to FIG. 5, one embodiment of a method for determining the region R to be avoided is shown. In step 300, a surgeon or other medical professional creates a surgical plan for the patient. The surgical plan identifies the surgical procedure to be performed and the treatment to be undertaken. The surgical plan is often based on pre-operative images, such as images taken from MRI or CT scans, which are converted into a 3-D virtual model VM of the patient's anatomy. The virtual object VB defining the target site TS to be treated during the surgical procedure is also generated and associated with the 3-D virtual model VM as part of the surgical plan.

In step 302, data relating to the virtual model VM and the virtual object VB, which defines the target volume of material to be treated at the target site TS, such as the target volume of bone to be removed, are transferred to the navigation computer 34 to be stored in the navigation computer 34.

In step 304, localizer data is then generated. The localizer data comprises data associated with the positions and orientations of the virtual model VM and the virtual object VB in the localizer coordinate system LCLZ. Image data is simultaneously being generated in step 306 so that at each time step during navigation, there is corresponding localizer data and image data. The image data comprises the point cloud 202 which comprises the position and orientation of surfaces in the field of view of the vision device 72, including surfaces of the target site TS and surfaces outside of the target site TS.

In step 308, the data merge module 101 of the navigation computer 34 evaluates the localizer data and the image data. In particular, the data merge module 101 merges data points from the image data (e.g., the point cloud 202) with data points from the localizer data (e.g., data points for the virtual object VB). In step 310, the data merge module 101 then identifies all of the data points from the image data that fall outside of the virtual object VB. This remaining data set yields the region R to be avoided, which is then saved in memory in the navigation computer 34 as the second virtual object VR to be avoided by the surgical instrument 30. In step 312, the user operates the surgical instrument 30, either manually, or robotically, to remove the target volume of tissue from the target site, while avoiding the region R. The steps 304-312 repeat for each processing time step during navigation until the surgical procedure is complete, e.g., until all the tissue has been removed from the target site TS. As a result, the method is able to compensate for changes to the region R during the surgical procedure.

In other embodiments, it should be appreciated that the systems and methods described herein for merging localizer data and image data could similarly be performed to generate other types of virtual objects, other than virtual objects that define regions to be avoided, like the region R. For instance, the localizer data and the image data could be merged to yield virtual objects that define target sites, such as volumes of material to be removed, desired trajectories for the surgical instrument 30, and the like. Additionally, the image data and the localizer data could be merged for other purposes.

As will be appreciated by one skilled in the art, aspects of the present embodiments may take the form of a computer program product embodied in one or more computer readable medium(s) having computer readable program code embodied thereon. Computer software including instructions or code for performing the methodologies described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:
1. A surgical system, comprising:
a localizer configured to generate localizer data associated with a bone;
a vision device configured to generate, in a coordinate system of the vision device, image data associated with the bone and an environment of the bone within a field-of-view of the vision device;
a robotic manipulator configured to support and move a surgical instrument; and
one or more controllers being configured to:
associate a virtual object with the bone;
determine a position and orientation of the virtual object based on the localizer data;
merge the image data and the localizer data associated with the bone into a common coordinate system; and
control the robotic manipulator based on an output of merging the image data and the localizer data.
2. The surgical system of claim 1, wherein:
the virtual object includes a 3D model of the bone;
the image data includes a 3D surface image of the bone; and
the one or more controllers are configured to merge the 3D model of the bone with the 3D surface image of the bone.
3. The surgical system of claim 1, wherein the one or more controllers are configured to control the robotic manipulator to manipulate the bone with the surgical instrument based on the output of merging the image data and the localizer data.

4. The surgical system of claim 1, wherein the one or more controllers are configured to determine a volume of the bone removed based on the output of merging the image data and the localizer data.

5. The surgical system of claim 1, wherein the one or more controllers are configured to determine a trajectory of the surgical instrument based on the output of merging the image data and the localizer data.

6. The surgical system of claim 1, wherein the one or more controllers are configured to:
identify an object based on the output of merging the image data and the localizer data; and
control the robotic manipulator relative to the object.

7. The surgical system of claim 6, wherein the object is one to be avoided by the surgical instrument.

8. The surgical system of claim 6, wherein the object is the bone.

9. The surgical system of claim 1, wherein the one or more controllers are configured to:
identify data points in the image data that have coordinates located outside of the virtual object; and
associate a second virtual object with the identified data points in the image data that have coordinates located outside of the virtual object.

10. The surgical system of claim 1, wherein the vision device is mounted to an adjustable arm.

11. A method of operating a surgical system, the surgical system comprising a localizer configured to generate localizer data associated with a bone, a vision device configured to generate, in a coordinate system of the vision device, image data associated with the bone and an environment of the bone within a field-of-view of the vision device, a robotic manipulator configured to support and move a surgical instrument, and one or more controllers, the method comprising:
associating, with the one or more controllers, a virtual object with the bone;
determining, with the one or more controllers, a position and orientation of the virtual object based on the localizer data;
merging, with the one or more controllers, the image data and the localizer data associated with the bone into a common coordinate system; and
controlling, with the one or more controllers, the robotic manipulator based on an output of merging the image data and the localizer data.

12. The method of claim 11, wherein the virtual object includes a 3D model of the bone and the image data includes a 3D surface image of the bone, the method comprising:
merging, with the one or more controllers, the 3D model of the bone with the 3D surface image of the bone.

13. The method of claim 11, comprising:
controlling, with the one or more controllers, the robotic manipulator for manipulating the bone with the surgical instrument based on the output of merging the image data and the localizer data.

14. The method of claim 11, comprising:
determining, with the one or more controllers, a volume of the bone removed based on the output of merging the image data and the localizer data.

15. The method of claim 11, comprising:
determining, with the one or more controllers, a trajectory of the surgical instrument based on the output of merging the image data and the localizer data.

16. The method of claim 11, comprising:
identifying, with the one or more controllers, an object based on the output of merging the image data and the localizer data; and
controlling, with the one or more controllers, the robotic manipulator relative to the object.

17. The method of claim 16, wherein the object is one to be avoided by the surgical instrument.

18. The method of claim 16, wherein the object is the bone.

19. The method of claim 11, comprising:
identifying, with the one or more controllers, data points in the image data that have coordinates located outside of the virtual object; and
associating, with the one or more controllers, a second virtual object with the identified data points in the image data that have coordinates located outside of the virtual object.

20. The method of claim 11, wherein the vision device is mounted to an adjustable arm, the method comprising:
adjusting a pose of the vision device with the adjustable arm.

* * * * *